United States Patent [19]

Smith et al.

[11] Patent Number: 4,874,784

[45] Date of Patent: Oct. 17, 1989

[54] QUATERNARY AMMONIUM COMPOUNDS

[75] Inventors: Kim R. Smith; James E. Borland; Joe D. Sauer, all of Baton Rouge, La.

[73] Assignee: Ethyl Corporation, Richmond, Va.

[21] Appl. No.: 312,125

[22] Filed: Feb. 17, 1989

Related U.S. Application Data

[60] Division of Ser. No. 910,417, Sep. 22, 1986, Pat. No. 4,824,867, and a continuation-in-part of Ser. No. 894,938, Aug. 8, 1986, and a continuation-in-part of Ser. No. 782,353, Oct. 1, 1985.

[51] Int. Cl.$^4$ ............................................. A01N 41/02
[52] U.S. Cl. ..................................... 514/517; 514/642
[58] Field of Search .................................... 514/517

[56] References Cited

U.S. PATENT DOCUMENTS 3,639,629  2/1972  Szabo et al. ......................... 514/517

*Primary Examiner*—Allen J. Robinson

[57] ABSTRACT

Quarternary ammonium compounds have the formula $R^1R^2R^3N^+(CH_2)_mY\ X^-$ wherein $R^1$ is an alkyl containing 8–20 carbon atoms, $R^2$ is an alkyl containing 8–20 carbon atoms or methyl or ethyl, $R^3$ is methyl or ethyl, m is an integer from 1–6, X is an anion and Y is a group having the structure $-Z$, $-OH$, $-OR^4$, $-OC(O)R^5$, $-CN$, $-O-S(O)(O)-OQ$, $-C(O)OR^6$, $-C\equiv CH$, $-SR^7$, $-S(O)(O)R^8$, $-S(O)R^9$, $-NR^{10}R^{11}$ and $-CH=CH_2$ wherein $R^4$, $R^5$, $R^6$, $R^7$, $R^8$, $R^9$, $R^{10}$, $R^{11}$ are alkyls containing 1–12 carbon atoms or are phenyl and Z is halogen and Q is hydrogen or a cation having been found to be very effective bactericides.

9 Claims, No Drawings

QUATERNARY AMMONIUM COMPOUNDS

This application is a division of application Ser. No. 910,417, filed Sept. 22, 1986 now U.S. Pat. No. 4,824,867, is a continuation-in-part of application Ser. No. 782,353 filed Sept. 30, 1985.

BACKGROUND OF THE INVENTION

Quaternary ammonium compounds referred to as "quats", are nitrogen compounds having four groups bonded to a nitrogen atom by a covalent C-N bond. The nitrogen atom has a positive charge which requires a counter anion or a balancing negative charge in the quat compound itself. Quats can be easily made by reacting a compound having a covalent halogen atom with a tert-amine.

SUMMARY OF THE INVENTION

According to the present invention a series of quats has been found which are effective in inhibiting the growth of bacteria and which have unique, highly desirable foam profiles.

DESCRIPTION OF THE PREFERRED EMBODIMENTS

A preferred embodiment of the invention is a method of inhibiting the growth of bacteria, said method comprising contacting said bacteria with a bacteriostatic amount of a quaternary ammonium compound having the formula

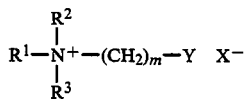

wherein $R^1$ is an alkyl containing 8-20 carbon atoms, $R^2$ is an alkyl containing 8-20 carbon atoms or is a methyl or ethyl group, $R^3$ is methyl or ethyl, m is an integer from 1 to 6, X is an anion and Y is selected from the group consisting of

—Z
—OH
—OR$^4$

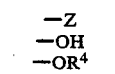

—CN

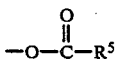

—C≡CH

—S—R$^7$

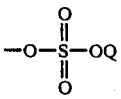

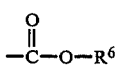

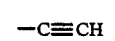

—CH=CH$_2$ wherein $R^4$, $R^5$, $R^6$, $R^7$, $R^8$, $R^9$, $R^{10}$ and $R^{11}$ are alkyls containing 1-12 carbon atoms or phenyl, Z is halogen and Q is H or a cation.

For the sake of simplifying the following disclosure the chemical group:

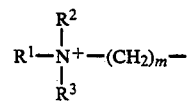

will be represented by the letter "A38". Thus the first group of bacteriostats have the structure A—Z X⁻ wherein Z is halogen, chlorine, bromine, fluorine or iodine. The more preferred halogens are chlorine and bromine. Representative examples of these quats are:
decyl dimethyl 2-bromoethyl ammonium chloride;
dodecyl dimethyl 2-chloroethyl ammonium bromide;
didecyl ethyl 3-bromoethyl ammonium chloride;
octadecyl dimethyl 4-chlorobutyl ammonium bromide;
hexadecyl diethyl 2-bromoethyl ammonium bromide;
dioctyl methyl 6-bromohexyl ammonium bromide;
eicosyl diethyl 2-bromoethyl ammonium bromide; and the like.

More preferably $R^1$ is an alkyl containing 8-20 carbon atoms, $R^2$ and $R^3$ are methyl, Z is chlorine or bromine and m is 2. Examples of these more preferred compounds are:
octyl dimethyl 2-chloroethyl ammonium chloride;
nonyl dimethyl 2-bromoethyl ammonium bromide;
decyl dimethyl 2-bromoethyl ammonium bromide;
octadecyl dimethyl 2-chloroethyl ammonium chloride;
dodecyl dimethyl 2-bromoethyl ammonium bromide;
hexadecyl dimethyl 2-bromoethyl ammonium chloride;
tetradecyl dimethyl 2-chloroethyl ammonium chloride;
tetradecyl dimethyl 2-bromoethyl ammonium bromide;
octadecyl dimethyl 2-chloroethyl ammonium chloride;
eicosyl dimethyl 2-bromoethyl ammonium bromide; and the like.

Another group of bacteriostats of the present invention are those having the structure A—N⁺R¹R²R³2X⁻. Example of these compounds are:
N,N'-didodecyl-N,N,N',N'-tetramethyl ethylene diammonium dibromide;
N,N'-dioctadecyl-N,N,N'N'-tetraethyl-1,4-butane diammonium dichloride;
N,N'-dioctyl-N,N,N',N'-tetramethyl-1,6-hexane diammonium dibromide;
N,N'-dieicosyl-N,N,N',N'-tetramethyl ethylene diammonium dichloride; and the like.

As with the previous group, the more preferred compounds are those in which $R^1$ is a C$_{8-20}$ alkyl, $R^2$ and $R^3$ are methyl, m is 2 and X is chlorine or bromine. Some further examples of these are:
N,N'-dioctyl-N,N,N',N'-tetramethyl ethylene diammonium dibromide;

N,N'-didecyl-N,N,N',N'-tetramethyl ethylenediammonium dichloride;
N,N'-dioctadecyl-N,N,N',N'-tetramethyl ethylenediammonium dichloride;
N,N'-ditetradecyl-N,N,N',N'-tetramethyl ethylenediammonium dibromide;
N,N'-dioctyl-N,N,N',N'-tetramethyl ethylenediammonium dichloride;
N,N'-didodecyl-N,N,N',N'-tetramethyl ethylenediammonium dichloride;
N,N'-dieicosyl-N,N,N',N'-tetramethyl ethylenediammonium bromide; and the like.

The foregoing two classes of compounds can be made by reacting the appropriate tert-amine having the structure $NR^1R^2R^3$ with a dihaloalkane such as ethylene dibromide. The reaction is conducted at a temperature of about 20°-100° C. using about 1 mole of tert-amine for each equivalent of halogen atom which is desired to be quaternerized. In other words to replace one halogen of the dihaloalkane 1 mole of tert-amine would be used whereas to replace both halogens of 1 mole of dihaloalkane, 2 moles of tert-amine would be used. Typical preparations of these compounds is shown in the following examples.

EXAMPLE 1

In a 5 liter 3-neck flask was placed 540.19 grams of decyldimethyl amine, 530.6 grams of ethylene dibromide and 1600 grams of ethyl acetate solvent. The mixture was stirred and heated under nitrogen for 24 hours. It was then diluted with isopropanol and then cooled to cause precipitation at 0° C. of the product, decyldimethyl(2-bromoethyl)ammonium bromide.

EXAMPLE 2

In a 500 mL 3-neck flask was placed 72.1 grams of decyldimethylamine, 35.42 grams of ethylene dibromide and 71.7 grams of ethyl acetate solvent. The mixture was stirred and heated under nitrogen at 90° C. and held at this temperature for 24 hours. The mixture was then cooled to 5° C. to precipitate N,N'-didecyl-N,N,N',N'-tetramethylethylenediammonium bromide which was recovered by filtration.

The next class of bacteriostats are those having the structure A—OH X⁻. Some examples of these are:
didodecyl methyl 3-hydroxypropyl ammonium iodide;
octadecyl diethyl 6-hydroxyhexyl ammonium fluoride; and the like.

The more preferred compounds of this class are those in which $R^1$ is a $C_{8-20}$ alkyl, $R^2$ and $R^3$ are methyl, m is 2 and X is chlorine or bromine. Examples of these preferred compounds are:
octyl dimethyl 2-hydroxyethyl ammonium bromide;
dodecyl dimethyl 2-hydroxyethyl ammonium chloride;
decyl dimethyl 2-hydroxyethyl ammonium chloride;
tetradecyl dimethyl 2-hydroxyethyl ammonium bromide;
eicosyl dimethyl 2-hydroxyethyl ammonium chloride;
tetradecyl dimethyl 2-hydroxyethyl ammonium chloride;
eicosyl dimethyl 2-hydroxyethyl ammonium bromide; and the like.

These compounds can be readily made by reacting a halo alcohol, $X(CH_2)_m$—OH, with a tert-amine, $R^1R^2R^3N$. The reaction is usually conducted in an inert solvent under nitrogen at elevated temperatures for a period to essentially complete quaternerization of the amine which can be followed by disappearance of the amine group. The following example shows the preparation of the hydroxyalkyl quats.

EXAMPLE 3

In a reaction vessel was placed 17.37 grams of 2-bromo ethanol, 27.8 grams of dodecyl dimethyl amine and 41.3 grams of methylethyl ketone solvent. The mixture was stirred at reflux (approx. 78° C.) under nitrogen for about 4 hours. It was then cooled and a precipitate formed which was identified as dodecyl dimethyl 2-hydroxyethyl ammonium bromide. This product was recovered by filtration.

It was also discovered that the above reaction is catalyzed by the inclusion of a small amount of potassium iodide when a trace of water is included as a co-catalyst. As little as 0.05 up to 0.5 parts by weight or more of potassium iodide per 100 parts of tert-amine are effective. The following example shows this effect.

EXAMPLE 4

In a reaction vessel was placed 32.99 grams of dodecyl dimethyl amine, 0.03 grams KI, 0.3 mL water and 15 mL 2-chloro ethanol. While stirring under nitrogen, the mixture was heated to 100° C. After 3.5 hours, 30 mL of methylethyl ketone was added and after 5 hours 20 minutes an additional 70 mLs of methylethyl ketone was added to dissolve the quat that started to gel. The mixture was then cooled causing the product, dodecyl dimethyl 2-hydroxyethyl ammonium chloride to precipitate. Conversion was based upon amine consumption.

Another class of quats of this invention can be represented by the formula $$A—OR^4X^-$$

wherein $R^4$ is an alkyl containing about 1–12 carbon atoms or phenyl. Some examples of these compounds are:
octyl dimethyl 2-methoxyethyl ammonium bromide;
dioctadecyl methyl 2-butoxyethyl ammonium chloride;
didecyl ethyl 2-hexoxyethyl ammonium fluoride;
tetradecyl dimethyl 3-dodecyloxypropyl ammonium iodide;
octadecyl dimethyl 4-methoxybutyl ammonium bromide;
tetradecyl dimethyl 2-phenoxyethyl ammonium chloride; and the like.

More preferably $R^1$ is a $C_{8-20}$ alkyl, $R^2$ and $R^3$ are methyl groups, m is 2 and X is chlorine or bromine. Examples of these preferred compounds are:
octyl dimethyl 2-methoxyethyl ammonium chloride;
decyl dimethyl 2-ethoxyethyl ammonium bromide;
dodecyl dimethyl 2-propoxyethyl ammonium iodide;
tetradecyl dimethyl 2-butoxyethyl ammonium fluoride;
octadecyl dimethyl 2-dodecyloxyethyl ammonium bromide; and the like.

These compounds can be made by reacting an appropriate alkoxy alkyl halide (e.g. $R^4$—O—$(CH_2)_m$—X) with a tert-amine (e.g. $R^1R^2R^3N$) at an elevated temperature to form the alkoxyalkyl quat. The following example shows a typical synthesis.

EXAMPLE 5

In a 2 liter 3-neck reaction flask was placed 212.3 grams tetradecyl dimethyl amine, 86.49 grams 2-methoxyethyl chloride and 425.45 grams para-dioxane solvent. The mixture was refluxed for 48 hours, cooled to crystallize the product and the white crystalline product recovered by filtration and identified as tetradecyl dimethyl 2-methoxyethyl ammonium chloride.

Another group of compounds of the invention are those having the formula A—O—C(O)—R$^5$X$^-$ wherein R$^5$ is an alkyl group containing about 1-12 carbon atoms or phenyl. Representative examples of this embodiment are:

octyl dimethyl 2-acetyloxyethyl ammonium chloride;
tetradecyl diethyl dodecanoyloxyethyl ammonium chloride;
octadecyl dimethyl 3-propionyloxypropyl ammonium iodide;
dodecyl dimethyl benzoyloxyethyl ammonium chloride;
dioctyl methyl 3-acetyloxyhexyl ammonium bromide;
octadecyl dimethyl tridecanoyloxyethyl ammonium bromide; and the like.

In a more preferred embodiment, R$^1$ is a C$_{8-20}$ alkyl, R$^2$ and R$^3$ are methyl groups, R$^5$ is methyl, X is chlorine or bromine and m is 2. Some examples of these compounds are:

decyl dimethyl 2-acetyloxyethyl ammonium bromide;
decyl dimethyl 2-acetyloxyethyl ammonium chloride;
octyl dimethyl 2-acetyloxyethyl ammonium chloride;
octyl dimethyl 2-acetyloxyethyl ammonium bromide;
dodecyl dimethyl 2-acetyloxyethyl ammonium bromide;
tetradecyl dimethyl 2-acetyloxyethyl ammonium bromide;
octadecyl dimethyl 2-acetyloxyethyl ammonium chloride;
eicosyl dimethyl 2-acetyloxyethyl ammonium chloride.

These acyloxyalkyl quats can be made by reacting a haloalkyl alkanoate, X—(CH$_2$)$_m$—O—C(O)—R$^5$, with a tert-amine, R$^1$R$^2$R$^3$N. Preferably an inert solvent is used and the reaction is conducted under nitrogen at an elevated temperature up to reflux. The following examples illustrate how the compounds can be made.

EXAMPLE 6

In a glass reaction vessel under nitrogen was placed 78.25 grams of ethyl acetate solvent and 32.65 grams of 2-bromoethyl acetate. While stirring, 41.14 grams of dodecyl dimethyl amine was added dropwise. A slight exotherm was observed. Heat was applied and the temperature raised to reflux (approx. 89° C.) which was continued for 6 hours. The mixture was then cooled to −10° C. causing the product to precipitate. The product, dodecyl dimethyl acetyloxyethyl ammonium bromide, was recovered by filtration.

The above compounds can also be made by reacting an appropriate acyl halide, R$^5$C(O)Cl, with a hydroxyalkyl trialkyl quat, R$^1$R$^2$R$^3$N$^+$(CH$_2$)$_m$OH X$^-$. This method is shown in the following example.

EXAMPLE 7

In a reaction vessel was placed 13.14 grams of dodecyl dimethyl 2-hydroxyethyl ammonium bromide, 21.22 grams of acetone solvent and 4.72 grams of sodium carbonate. While stirring under nitrogen, 3.27 grams of acetyl chloride was added dropwise. Gas evolution occurred. The mixture was then refluxed (approx. 60° C.) for 6 hours. The solvent was removed under vacuum. The residue was extracted with isopropanol to dissolve the quat and the solution was filtered hot to remove sodium chloride and sodium carbonate. The filtrate was evaporated under vacuum leaving as the product dodecyl dimethyl acetyloxyethyl ammonium bromide. Still another embodiment of the invention are bacteriostats of the formula A—CN X$^-$. These can be exemplified by:

dioctyl methyl cyanomethyl ammonium bromide;
didecyl methyl 2-cyanopropyl ammonium chloride;
didodecyl methyl 5-cyanopentyl ammonium iodide;
octadecyl dimethyl 6-cyanohexyl ammonium fluoride;
eicosyl diethyl cyanoethyl ammonium chloride; and the like.

More preferably R$^1$ is a C$_{8-20}$ alkyl, R$^2$ and R$^3$ are methyl groups, m is 2 and X is chlorine or bromine. These are illustrated by:

octyl dimethyl 2-cyanoethyl ammonium chloride;
decyl dimethyl 2-cyanoethyl ammonium bromide;
dodecyl diethyl 2-cyanoethyl ammonium chloride;
tetradecyl dimethyl 2-cyanoethyl ammonium bromide;
octadecyl dimethyl 2-cyanoethyl ammonium bromide;
eicosyl dimethyl 2-cyanoethyl ammonium chloride;
decyl diethyl 2-cyanoethyl ammonium bromide; and the like.

This class of quats can be made by reacting an appropriate haloalkyl nitrile, hal—(CH$_2$)$_m$—CN, with a tert-amine, R$^1$R$^2$R$^3$N, in an inert solvent such as tetrahydrofuran, dioxane or diglyme and preferably under nitrogen and under substantially anhydrous conditions. The following example shows how the nitrile quats can be made.

EXAMPLE 8

In a reaction vessel was placed 130.5 grams of dioxane and 40.48 grams of dodecyl dimethyl amine. While stirring under nitrogen, 25.69 grams of 2-bromoethyl nitrile was added dropwise. An exotherm occurred raising the temperature to 40° C. and a white precipitate formed. The mixture was heated to reflux and held at reflux (approx. 95°-100° C.) for 2.5 hours. The mixture was then cooled and an additional 382.49 grams of paradioxane was added. The product, dodecyl dimethyl 2-cyanoethyl ammonium bromide, precipitated and was recovered by filtration.

In another embodiment of the invention the bacteriostat has the formula

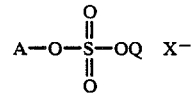

X$^-$ wherein Q is hydrogen or a cation. Suitable cations are the alkali metals (e.g. sodium, potassium), ammonium (NH$_4^+$) and the like. When Q is an alkali metal, the alkali metal cation can precipitate the X$^-$ anion so that the resultant quat is internally neutralized as follows:

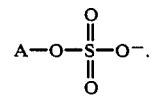

This internally neutralized sulfate quat is the equivalent of the same quat neutralized by an external anion and is within the scope of the invention. Some examples of these compounds are:

dioctyl methyl 2-hydrosulfatoethyl ammonium bromide;
nonyl dimethyl (sodium 4-sulfatobutyl) ammonium chloride;
octadecyl diethyl 2-hydrosulfatoethyl ammonium fluoride;
hexadecyl dimethyl 2-hydrosulfatobutyl ammonium bromide;
octyl dimethyl 2-sulfatoethyl ammonium bromide;
dodecyl dimethyl 2-sulfatoethyl ammonium chloride;
octadecyl dimethyl 3-sulfatopropyl ammonium bromide; and the like.

In a preferred embodiment, $R^1$ is a $C_{8-20}$ alkyl, $R^2$ and $R^3$ are methyl groups, m is 2 and X is chlorine or bromine. Representative examples of these compounds are:
octyl dimethyl 2-hydrosulfatoethyl ammonium chloride;
octyl dimethyl 2-hydrosulfatoethyl ammonium bromide;
decyl dimethyl 2-hydrosulfatoethyl ammonium bromide;
decyl dimethyl 2-sulfatoethyl ammonium chloride;
dodecyl dimethyl 2-hydrosulfatoethyl ammonium chloride;
dodecyl dimethyl 2-hydrosulfatoethyl ammonium bromide;
tetradecyl dimethyl 2-hydrosulfatoethyl ammonium bromide;
octadecyl dimethyl 2-sulfatoethyl ammonium chloride; and the like including the alkali metal salts.

One method of making these sulfate-substituted quats is to react chlorosulfonic acid, $ClSO_3H$, with the hydroxy quat A—OH $X^-$. This reaction is preferably conducted in an inert solvent under nitrogen at temperatures from 0° C. up to reflux. The following example illustrates the preparation of a sulfate quat.

EXAMPLE 9

In a reaction vessel was placed 29.45 grams of dodecyl dimethyl 2-hydroxyethyl ammonium bromide and 50 mLs of methylene chloride solvent. This was cooled to 5° C. and while stirring under nitrogen, 10.21 grams of chlorosulfonic acid was added dropwise over 15 minutes at 5°–10° C. Then 4.75 grams of sodium carbonate was added to neutralize the mixture and the orange solution was filtered. The methylene chloride was evaporated from the filtrate under vacuum leaving as the product a light tan solid identified as dodecyl dimethyl 2-sulfatoethyl ammonium bromide.

The sulfato quat can also be made by the direct sulfonation of the hydroxyalkyl quat, A—OH $X^-$, with $SO_3$. This is shown in the following example.

EXAMPLE 10

In a reaction vessel was placed 8.15 grams of dodecyldimethyl 2-hydroxyethyl ammonium bromide and 25 mLs of methylene chloride. This solution was stirred under nitrogen and cooled to 10° C. Then, 2.62 grams of liquid $SO_3$ was added dropwise at 10°–15° C. Unreacted $SO_3$ was then sparged from the flask with nitrogen. Sufficient sodium carbonate was added to neutralize acidity and the mixture was filtered. The filtrate was evaporated under vacuum eaving as the product dodecyl dimethyl sulfatoethyl ammonium bromide.

Another class of compounds of the invention are those having the formula A—C(O)—O—$R^6X^-$ wherein $R^6$ is an alkyl containing from 1 to about 12 carbon atoms or a phenyl group. Representative examples of these compounds are:
octyl dimethyl (2-acetic acid hexyl ester) ammonium bromide;
decyl diethyl (3-propionic acid phenyl ester) ammonium iodide;
octyl dimethyl (4-butyric acid hexyl ester) ammonium chloride;
hexadecyl diethyl (6-hexanoic acid butyl ester) ammonium fluoride; and the like.

The more preferred compounds are those in which $R^1$ is a $C_{8-20}$ alkyl, $R^2$ and $R^3$ are methyl groups, m is 1 or 2, and X is chlorine or bromine. Some examples of these preferred compounds are:
octyl dimethyl (2-acetic acid methyl ester) ammonium bromide;
decyl dimethyl (3-propionic acid octyl ester) ammonium chloride;
dodecyl dimethyl (2-acetic acid phenyl ester) ammonium bromide;
tetradecyl dimethyl (3-propionic acid butyl ester) ammonium chloride;
eicosyl dimethyl (2-acetic acid dodecyl ester) ammonium chloride; and the like.

These compounds can be made by reacting an appropriate haloalkanoate ester, X—$(CH_2)_m$—C(O)—$OR^6$, with a trialkyl amine, $R^1R^2R^3N$. The reaction is conducted in an inert solvent at an elevated temperature up to reflux. The following example illustrates the way these compounds are made.

EXAMPLE 11

In a reaction flask was placed 8.16 grams of methyl 3-bromopropionate and 20 mL methylethyl ketone. To this was added 11.26 grams of tetradecyl dimethyl amine and the mixture was refluxed for 6 hours. The reaction mixture was then cooled and the product, tetradecyl dimethyl (3-propionic acid methyl ester) ammonium bromide precipitated.

The ester quat can also be made by esterification of the appropriate betaine.

EXAMPLE 12

In a reaction flask was placed 20 grams of dodecyldimethyl betaine, 1.83 grams of phenol, 20 mLs of toluene and 1 mL of conc. HCl. This was heated to reflux and water was removed using a Dean-Stark water trap. Temperature gradually rose to 110° C. at which time no more water came off. After 4 hours the mixture was cooled and the product dodecyldimethyl (2-acetic acid phenyl ester) ammonium chloride precipitated and was recovered by filtration.

A still further group of bacteriostats of the invention are the alkyne quats having the structure A—C≡CH. In this application the compounds will be named as alkyne substituted quaternary ammonium compounds such that the compound

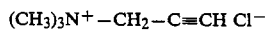

is named trimethyl 3-(1-propyne) ammonium chloride. Other examples of these acetylenic quats are:
octyl dimethyl 4-(1-butyne) ammonium iodide;
octadecyl dimethyl 6-(1-hexyne) ammonium fluoride;
didodecyl ethyl 3-(1-propyne) ammonium chloride; and the like.

The more preferred compounds of this class are those wherein $R^1$ is a $C_{8-20}$ alkyl, $R^2$ and $R^3$ are methyl groups, m is 1 and X is chlorine or bromine. Examples of these more preferred acetylenic quats are:
octyl dimethyl 3-(1-propyne) ammonium chloride;
decyl dimethyl 3-(1-propyne) ammonium bromide;
dodecyl dimethyl 3-(1-propyne) ammonium chloride;
tetradecyl dimethyl 3-(1-propyne) ammonium bromide;
octadecyl dimethyl 3-(1-propyne) ammonium chloride;
octyl dimethyl 3-(1-propyne) ammonium bromide;
dodecyl dimethyl 3-(1-propyne) ammonium bromide;
eicosyl dimethyl 3-(1-propyne) ammonium chloride;
and the like.

The acetylenic quats can be made by reacting the appropriate haloalkyne, $X-(CH_2)_m-C \equiv CH$ such as propargylbromide, with the appropriate tert-amine, $R^1R^2R^3N$. An inert solvent can be used. The following example illustrates how the acetylenic quats can be made.

EXAMPLE 13

In a reaction flask was placed 64.28 grams of octyl dimethyl amine and 90.17 grams of methylethyl ketone. With stirring and under a nitrogen atmosphere, 30.76 grams of propargyl chloride was added dropwise over a 30 minute period. The mixture was then heated to reflux (ca. 85° C.) and held at reflux for 1 hour. The product, octyl dimethyl 3-(1-propyne) ammonium chloride, stayed in solution upon cooling as a dark gold liquid.

Another embodiment of the invention is an alkylthio quat. These are compounds having the formula $A-S-R^7 X^-$ wherein $R^7$ is an alkyl containing 1 to about 12 carbon atoms or a phenyl group. Some examples of these compounds are:
octyl dimethyl methylthioethyl ammonium chloride;
octadecyl diethyl butylthioethyl ammonium bromide;
octadecyl dimethyl hexylthiobutyl ammonium iodide;
hexadecyl dimethyl decylthiohexyl ammonium fluoride;
dodecyl diethyl ethylthiopentyl ammonium bromide;
octyl dimethyl phenylthioethyl ammonium bromide;
didodecyl methyl phenylthiobutyl ammonium iodide; and the like.

The more preferred alkylthio quats of this embodiment are those in which $R^1$ is a $C_{8-20}$ alkyl, $R^2$ and $R^3$ are methyl groups, $R^7$ is alkyl, m is 1 and X is chlorine or bromine. Some examples of these more preferred compounds are:
octyl dimethyl methylthiomethyl ammonium bromide;
decyl dimethyl ethylthiomethyl ammonium chloride;
dodecyl dimethyl butylthiomethyl ammonium bromide;
tetradecyl dimethyl decylthiomethyl ammonium chloride;
dioctyl methyl methylthiomethyl ammonium chloride;
decyl dimethyl propylthiomethyl ammonium bromide;
dodecyl dimethyl butylthiomethyl ammonium chloride;
tetradecyl dimethyl dodecylthiomethyl ammonium bromide; and the like.

These alkylthio quats can be made by reacting an alkylthio alkyl halide, $R^7-S-(CH_2)m-hal$, with a tert-amine, $R^1R^2R^3N$, in an inert solvent at an elevated temperature of about 50° C. up to reflux. The reaction is preferably maintained under nitrogen Some of the alkylthio alkyl halides used in the preparation are stench compounds so due caution should be maintained. The preparation of a typical alkylthio quat is shown in the following example.

EXAMPLE 14

In a reaction vessel was placed 99.9 grams of methylethyl ketone, 70.02 grams of tetradecyl dimethyl amine and 30.9 grams of methylthiomethylchloride. The mixture was stirred and heated under nitrogen to reflux (c.a. 90° C.) and held at reflux for 6 hours It was then cooled and the product, tetradecyl dimethyl methylthiomethyl ammonium chloride precipitated as a yellow-white solid and was recovered by filtration.

The following example shows the preparation of an alkylthio quat without the use of a solvent.

EXAMPLE 15

In a glass reaction vessel was placed 86.52 grams of didecyl methyl amine. The amine was stirred under nitrogen and 29.07 grams of methylthiomethylchloride was added dropwise over 5 minutes. The mixture was then heated to 100° C. and stirred at 100° C. for 6 hours. On cooling the product, didecyl methyl methylthiomethyl ammonium chloride solidified.

A still further embodiment of the invention are the sulfone quats having the structure

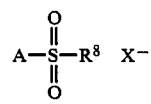

wherein $R^8$ is an alkyl containing 1 to about 12 carbon atoms or a phenyl group. Some examples of these compounds are:
decyl dimethyl methylsulfonomethyl ammonium chloride;
hexadecyl diethyl butylsulfonoethyl ammonium bromide;
octadecyl dimethyl hexylsulfonobutyl ammonium fluoride;
dioctyl ethyl decylsulfonohexyl ammonium iodide;
octyl dimethyl phenylsulfonoethyl ammonium chloride;
dodecyl dimethyl phenylsulfonopropyl ammonium bromide;
dioctyl ethyl phenylsulfonomethyl ammonium iodide; and the like.

Of the above sulfone quats, the more preferred are those in which $R^1$ is a $C_{8-20}$ alkyl, $R^2$ and $R^3$ are methyl groups, $R^8$ is alkyl, m is 1 and X is chlorine or bromine. Some examples of these compounds are:
octyl dimethyl methylsulfonomethyl ammonium chloride;
decyl dimethyl ethylsulfonomethyl ammonium bromide;
dodecyl dimethyl butylsulfonomethyl ammonium chloride;
tetradecyl dimethyl decylsulfonomethyl ammonium bromide;
octadecyl dimethyl methylsulfonomethyl ammonium chloride;
octyl dimethyl dodecylsulfonomethyl ammonium chloride;
decyl dimethyl propylsulfonomethyl ammonium bromide;
dodecyl dimethyl hexylsulfonomethyl ammonium chloride;
tetradecyl dimethyl octylsulfonomethyl ammonium bromide;

eicosyl dimethyl methylsulfonomethyl ammonium chloride; and the like.

The new compounds can be made by oxidizing the previous alkylthio quats using aqueous hydrogen peroxide. Care should be taken so that a large amount of unreacted hydrogen peroxide is not allowed to buildup in the reaction mixture. The following example shows the preparation of a typical sulfone substituted quat.

EXAMPLE 16

In a reaction vessel was placed 20.5 grams of the didecyl methyl methylthiomethyl ammonium chloride made in Example 17. This was heated to 60° C. to melt the quat and then 10.5 grams of 50% aqueous hydrogen peroxide was added dropwise over a 1 hour period with vigorous stirring. An exothermic reaction occurred. The reaction was then heated to 75° C. and held at this temperature for 4 hours forming a pale yellow liquid. On cooling the liquid gelled. Infrared confirmed the compound as being didecyl methyl methylsulfonomethyl ammonium chloride.

Another bacteristat of the invention can be represented by sulfoxide substituted quats which have the formula

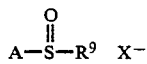

wherein $R^9$ is an alkyl containing about 1 to 12 carbon atoms or a phenyl group. These compounds can be exemplified by the following:
octyl dimethyl butylsulfoxomethyl ammonium chloride;
dodecyl dimethyl decylsulfoxoethyl ammonium bromide;
dioctyl ethyl octylsulfoxomethyl ammonium fluoride;
octadecyl dimethyl phenylsulfoxomethyl ammonium bromide;
eicosyl dimethyl dodecylsulfonomethyl ammonium iodide; and the like.

In a more preferred embodiment of the sulfoxide quat, $R^1$ is a $C_{8-20}$ alkyl, $R^2$ and $R^3$ are methyl groups, $R^9$ is alkyl, m is 1 and X is chlorine or bromine. Representative examples of this more preferred class of compounds are:
octyl dimethyl methylsulfoxomethyl ammonium chloride;
decyl dimethyl ethylsulfoxomethyl ammonium bromide;
dodecyl dimethyl butylsulfoxomethyl ammonium chloride;
tetradecyl dimethyl decylsulfoxomethyl ammonium bromide;
octyl dimethyl methylsulfoxomethyl ammonium bromide;
decyl dimethyl ethylsulfoxomethyl ammonium chloride;
dodecyl dimethyl butylsulfoxomethyl ammonium bromide;
eicosyl dimethyl decylsulfoxomethyl ammonium chloride; and the like.

The sulfoxide quats can be made by the oxidation of the alkylthio quats using the proper stoichiometry to oxidize the sulfur to the tetravalent state. The preparation of a sulfoxide quat is shown in the following example.

EXAMPLE 17

In a glass reaction flask was placed 21.95 grams of the didecyl methyl methylthiomethyl ammonium chloride from Example 17. This was warmed to 60° C. to melt the quat and 4.03 grams of 50% aqueous hydrogen peroxide was added dropwise over 8 minutes at 60° C. with vigorous stirring. The mixture was then heated to 75° C. and held at 75° C. for 2 hours. On cooling the product, didecyl methyl methylsulfoxomethyl ammonium chloride was recovered as a brown liquid.

Another useful bacteriostat of the present invention are compounds having the formula

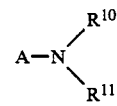

wherein $R^{10}$ and $R^{11}$ are alkyls containing 1–12 carbon atoms or are phenyl. Examples of these compounds are:
octyl diethyl dimethylaminoethyl ammonium chloride;
decyl dimethyl dimethylaminoethyl ammonium bromide;
dodecyl dimethyl dimethylaminopropyl ammonium chloride;
tetradecyl dimethyl (N-methyl-N-phenyl aminobutyl) ammonium iodide;
octadecyl diethyl (N-methyl-N-dodecyl aminopropyl) ammonium bromide;
eicosyl diethyl dimethylaminopropyl ammonium bromide.

The more preferred compounds are those in which $R^1$ is an alkyl containing 8–20 carbon atoms, $R^2$ and $R^3$ are methyl, m is 2 or 3, X is chloride or bromide and $R^{10}$ and $R^{11}$ are alkyl. Examples of these compounds are:
octyl dimethyl dimethylaminoethyl ammonium chloride;
dodecyl dimethyl diethylaminopropyl ammonium bromide;
tetradecyl dimethyl dimethylaminopropyl ammonium chloride;
hexadecyl dimethyl didecylaminoethyl ammonium bromide;
eicosyl dimethyl didodecylaminobutyl ammonium chloride.

These compounds can be made by reacting the compound A—Br—X with the secondary amine $HNR^{10}R^{11}$ in an aqueous solvent. This is shown in the following example.

EXAMPLE 18

In a glass reaction vessel was placed 69.3 grams of water and 30.8 grams of decyl dimethyl bromoethyl ammonium bromide. Dimethyl amine was bubbled into the liquid. An exothermic reaction set in carrying the temperature up to 59° C. forming decyl dimethyl dimethylaminoethylammonium bromide.

Another useful class of bacteriostats are the compounds having the formula A—CH=CH₂. Examples of these are:
dioctyl methyl allyl ammonium chloride;
didodecyl ethyl (4-butenyl) ammonium bromide;
eicosyl diethyl 6-hexenyl ammonium iodide;
octyl diethyl allyl ammonium bromide;
dodecyl dimethyl (4-butenyl) ammonium chloride;

octadecyl diethyl (5-pentenyl) ammonium iodide.

The more preferred alkenyl quats are those in which $R^1$ is an alkyl containing 8-20 carbon atoms, $R^2$ and $R^3$ are methyl, m is 1 and X is chloride or bromide. Some examples of these are:

octyl dimethyl allyl ammonium bromide;
decyl dimethyl 4-butenyl ammonium chloride;
dodecyl dimethyl 6-hexenyl ammonium chloride;
tetradecyl dimethyl allyl ammonium chloride;
hexadecyl dimethyl allyl ammonium bromide;
eicosyl dimethyl 5-pentenyl ammonium chloride.

These compounds are made by reacting an alkenyl halide hal—$(CH_2)_m$—$CH=CH_2$ with a tert-amine $R^1R^2R^3N$ in an inert solvent such as methyl ethyl ketone (MEK) or ethyl acetate. The following examples show the synthesis.

EXAMPLE 19

In a reaction vessel was placed 104.8 grams of MEK, 95.2 grams of octadecyl dimethyl amine and 39.8 grams of allylbromide. The solution was stirred at 80° C. for 2 hours. The mixture was cooled and filtered to recover octadecyl dimethyl allyl ammonium bromide as a white powder.

EXAMPLE 20

In a reaction vessel was placed 77.5 grams tetradecyl dimethyl amine, 108.1 grams ethyl acetate and 40.4 grams of allylbromide. This was refluxed under nitrogen for 6 hours. The mixture was cooled and filtered to recover tetradecyl dimethyl allyl ammonium bromide as a white solid.

Tests were conducted to determine the bactericidal properties of the quats. The test organisms were *Staphylococcus aureus* (*S. aureus*), *Escherichia coli* (*E. coli*), *Pseudomonas aerucinosa* (*Ps. aerucinosa*), *Candida albicaus* (*C. albicaus*). A nutrient broth was prepared by boiling 5 grams beef extract, 10 grams peptone and 5 grams NaCl in 1000 ml distilled water (FDA formula for germicide testing). The broth was cooled, adjusted to pH 6.8-6.9 and 8.9-9.9 ml quantities placed in bacteriological tubes. The tubes were capped and sterilized at 15 psig steam pressure for 20 minutes.

The test compounds are dissolved in distilled water at 10 times the desired test concentration and then 1 ml of the solution is added to 9 ml of the sterile nutrient broth. Three tubes are prepared for each test organism. The tubes are then inoculated with 0.1 ml of the test organism culture. One baseline tube containing the test compound solution is left uninoculated. The tubes were incubated 24 hours and the turbidity is measured using a Coleman Jr. Spectrophotometer and recorded as percent transmission. The transmission of the inoculated tube is corrected by subtracting any loss of transmission in the uninoculated tubes.

A decrease in light transmission of greater than 15 percent was recorded as non-inhibitory. A decrease of 9-15 percent was slightly inhibitory. A decrease of 3-8 percent is considered moderately inhibitory. Decrease of less than 3% is considered completely inhibitory.

The test compounds were as follows:
A. tetradecyldimethyl (2-methoxyethyl) ammonium chloride
B. tetradecyldimethyl methylthiomethyl ammonium chloride
C. tetradecyl dimethyl (2-hydroxyethyl) ammonium chloride
D. tetradecyl dimethyl (3-propenyl) ammonium chloride.

| Ps. Aeruginosa | | |
|---|---|---|
| Compound | Conc. (ppm) | Result[1] |
| A | 65 | mod. inhibition |
| A | 50 | mod. inhibition |
| A | 35 | slt. inhibition |
| A | 20 | non-inhibition |
| B | 65 | comp. inhibition |
| B | 50 | comp. inhibition |
| B | 35 | comp. inhibition |
| B | 20 | non-inhibition |
| C | 65 | comp. inhibition |
| C | 50 | comp. inhibition |
| C | 35 | comp. inhibition |
| C | 20 | non-inhibition |
| D | 65 | slt. inhibition |
| D | 50 | non-inhibition |
| D | 35 | non-inhibition |
| D | 20 | non-inhibition |

| S. Aureus | | |
|---|---|---|
| Compound | Conc. (ppm) | Result[1] |
| A | 8 | mod. inhibition |
| A | 4 | mod. inhibition |
| A | 2 | slt. inhibition |
| A | 1 | non-inhibition |
| B | 8 | comp. inhibition |
| B | 4 | comp. inhibition |
| B | 2 | comp. inhibition |
| B | 1 | comp. inhibition |
| C | 8 | comp. inhibition |
| C | 4 | comp. inhibition |
| C | 2 | comp. inhibition |
| C | 1 | non-inhibition |
| D | 8 | comp. inhibition |
| D | 4 | comp. inhibition |
| D | 2 | comp. inhibition |
| D | 1 | comp. inhibition |

| E. Coli | | |
|---|---|---|
| Compound | Conc. (ppm) | Result[1] |
| A | 13.33 | comp. inhibition |
| A | 10.0 | mod. inhibition |
| A | 6.66 | slt. inhibition |
| A | 3.33 | non-inhibition |
| B | 13.33 | comp. inhibition |
| B | 10.0 | comp. inhibition |
| B | 6.66 | mod. inhibition |
| B | 3.33 | non-inhibition |
| C | 13.33 | slt. inhibition |
| C | 10.0 | slt. inhibition |
| C | 6.66 | non-inhibition |
| C | 3.33 | non-inhibition |
| D | 13.33 | comp. inhibition |
| D | 10.0 | mod. inhibition |
| D | 6.66 | non-inhibition |
| D | 3.33 | non-inhibition |

| C. Albicaus | | |
|---|---|---|
| Compound | Conc. (ppm) | Result[1] |
| A | 13.33 | comp. inhibition |
| A | 10.0 | comp. inhibition |
| A | 6.66 | comp. inhibition |
| A | 3.33 | comp. inhibition |
| B | 13.33 | comp. inhibition |
| B | 10.0 | comp. inhibition |
| B | 6.66 | comp. inhibition |
| B | 3.33 | comp. inhibition |
| C | 13.33 | comp. inhibition |
| C | 10.0 | mod. inhibition |
| C | 6.66 | slt. inhibition |
| C | 3.33 | slt. inhibition |
| D | 13.33 | comp. inhibition |
| D | 10.0 | comp. inhibition |
| D | 6.66 | comp. inhibition |

| -continued | | |
|---|---|---|
| D | 3.33 | comp. inhibition |

[1] comp. means complete
mod. means moderate
slt. means slight

Further tests were conducted to measure bactericidal properties. These tests called the "Alberto-Culver Antimicrobiol Test" determines the concentration of each test compound required to completely inhibit the growth of a organism. The test organism was *S. aureus*. The test compounds were:

F. tetradecyl dimethyl propargyl ammonium chloride;
G. tetradecyldimethyl (20 methoxyethyl) ammonium chloride;
H. tetradecyl dimethyl (2-hydroxyethyl) ammonium chloride;
I. tetradecyl dimethyl allyl ammonium bromide;
J. tetradecyl dimethyl methylthiomethyl ammonium chloride;
K. tetradecyl dimethyl 2-acetyloxyethyl ammonium bromide.

The following table gives the minimum concentration of each additive that still completely inhibited organism growth.

| Compound | Minimum Conc. (ppm) |
|---|---|
| F | 50 |
| G | 50 |
| H | 125 |
| I | 50 |
| J | 50 |
| K | 125 |

As stated previously, the present bacteriostats have either much lower foam profiles or much higher foam profiles than the prior art quaternary bacteriostats. This allows them to be used without foam suppressant or foam enhancing co-additives in formulations used as toilet bowl cleaners and swimming pool algicide. This property of the present bacteriostats has been done using the standard Ross-Miles foam test.

We claim:

1. A method of inhibiting the growth of bacteria, said method comprising contacting said bacteria with a bactericidal amount of a quaternary ammonium compound having the formula:

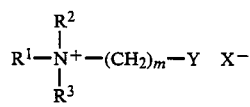

wherein $R^1$ is an alkyl containing 8-10 carbon atoms, $R^2$ is an alkyl containing 8-20 carbon atoms, methyl or ethyl, $R^3$ is methyl or ethyl, m is an integer from 1 to 6, X is an anion and Y is wherein Q is H or a cation

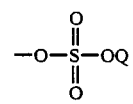

2. The method of claim 1 wherein said quaternary ammonium compound is dioctyl methyl 2-hydrosulfatoethyl ammonium bromide.
3. The method of claim 1 wherein said quaternary ammonium compound is nonyl dimethyl (sodium 4-sulfatobutyl) ammonium chloride.
4. The method of claim 1 wherein said quaternary ammonium compound is octadecyl diethyl 2-hydrosulfatoethyl ammonium fluoride.
5. The method of claim 1 wherein said quaternary ammonium compound is dodecyl dimethyl 2-sulfatoethyl ammonium chloride.
6. The method of claim 1 wherein said quaternary ammonium compound is octyl dimethyl 2-hydrosulfatoethyl ammonium chloride.
7. The method of claim 1 wherein said quaternary ammonium compound is decyl dimethyl 2-hydrosulfatoethyl ammonium bromide.
8. The method of claim 1 wherein said quaternary ammonium compound is dodecyl dimethyl 2-hydrosulfatoethyl ammonium bromide.
9. The method of claim 1 wherein said quaternary ammonium compound is tetradecyl dimethyl 2-hydrosulfatoethyl ammonium chloride.